(12) United States Patent
Zhou et al.

(10) Patent No.: US 6,265,179 B1
(45) Date of Patent: Jul. 24, 2001

(54) DETECTION OF PHOSPHATE USING COUPLED ENZYMATIC REACTIONS

(75) Inventors: Mingjie Zhou; Richard P. Haugland, both of Eugene, OR (US)

(73) Assignee: Molecular Probes, Inc., Eugene, OR (US)

( * ) Notice: Subject to any disclaimer, the term of this patent is extended or adjusted under 35 U.S.C. 154(b) by 0 days.

(21) Appl. No.: 09/495,882

(22) Filed: Feb. 1, 2000

(51) Int. Cl.[7] ............ C12Q 1/28; C12Q 1/42; C12Q 1/26; C12Q 1/54

(52) U.S. Cl. ............ 435/28; 435/21; 435/25; 435/975; 435/14; 435/968

(58) Field of Search ............ 435/28, 21, 25, 435/975, 14, 968

(56) References Cited

U.S. PATENT DOCUMENTS

| | | | |
|---|---|---|---|
| 4,159,923 | 7/1979 | Pierre et al. | 435/28 |
| 4,384,042 | 5/1983 | Miike et al. | 435/28 |
| 4,547,280 | 10/1985 | Karasawa et al. | 435/28 |
| 4,916,058 | 4/1990 | Aoyama et al. | 435/28 |
| 5,459,268 * | 10/1995 | Haugland et al. | 546/37 |
| 5,496,708 | 3/1996 | Kawasaki et al. | 435/28 |

FOREIGN PATENT DOCUMENTS

| | | |
|---|---|---|
| 0 252 747 B1 | 7/1987 | (EP) . |
| 0 629 705 A2 | 6/1994 | (EP) . |
| 0 727 495 A2 | 2/1996 | (EP) . |
| 56-021599 | 2/1981 | (JP) . |
| WO 99/01768 | 1/1999 | (WO) . |

OTHER PUBLICATIONS

Brune et al; Biochemistry, V.33(27), p8262, Jul., 1994, (Abstract Onyly).*
Zhou et al, Anal. Bioch 253, 162–168 (1997).
Conrath et al, Analytica Chimica Acta 309, 47–52 (1995).
Sugiura et al, Japan J. Clin, Chem. vol. 11 No. 2, 83–87(1982).
Ikebukuro et al, Journal of Biotechnology 48, 67–72 (1996).
Zoppi et al, Clinical Chemistry, vol. 31 No. 7, (1985).
Adam et al, Clinical Chemistry, vol. 30 No. 10, (1984).
Haugland, Molecular Probes Handbook, 236–237, (1996).
Bioprobes 27, p. 14 (1998).

* cited by examiner

*Primary Examiner*—Louise N. Leary
(74) *Attorney, Agent, or Firm*—Allegra J. Helfenstein

(57) ABSTRACT

Inorganic phosphate may be detected and optionally quantified via the coupling of a phosphate-dependent enzymatic reaction with an enzyme system that generates hydrogen peroxide in the presence of a chromogenic or fluorogenic peroxidase substrate. Phosphate consuming or phosphate-producing enzymes or their substrates may also be detected and/or quantified, including pyrophosphatase enzymes or pyrophosphatase.

46 Claims, 2 Drawing Sheets

DETECTION OF PHOSPHATE USING COUPLED ENZYMATIC REACTIONS

FIELD OF THE INVENTION

The invention relates to detection and optionally the quantification of phosphate, and other analytes related to the production or consumption of inorganic phosphate. The invention utilizes the coupling of a phosphate-dependent enzymatic reaction with an enzyme system that generates hydrogen peroxide in the presence of a chromogenic and/or fluorogenic peroxidase substrate.

BACKGROUND

Inorganic phosphate ion ($PO_4^{3-}$, or $P_i$) is a critical component in many biological systems, and so a variety of assays have been developed for the detection and/or quantification of inorganic phosphate. While previous methods have utilized coupled enzyme reactions, none of the previously described methods for detecting or quantitating inorganic phosphate utilized the fluorogenic peroxidase substrates of the present invention, and did not offer the sensitivity and accuracy of the methods of the instant invention.

The instant invention describes highly sensitive methods for the enzymatic determination of inorganic phosphate, including the consumption or production of phosphate, by coupling the system of interest to a probe for hydrogen peroxide. The system of interest is coupled enzymatically to a reaction producing hydrogen peroxide, which is coupled to a peroxidase enzyme reaction in the presence of a chromogenic or fluorogenic substrate. Unlike the methods previously used for detecting and monitoring phosphate, the methods of the instant invention are highly sensitive, may be utilized at wavelengths that are more compatible with biological samples, may be carried out at physiological pH, and permit a continuous assay. Given its high sensitivity and one-step procedure, the method of the invention is a valuable tool for measuring a variety of phosphate-dependent enzymes in biological samples, particularly as a microplate-based assay for high-throughput applications.

SUMMARY OF THE INVENTION AND DESCRIPTION OF THE PREFERRED EMBODIMENTS

Figure 1:
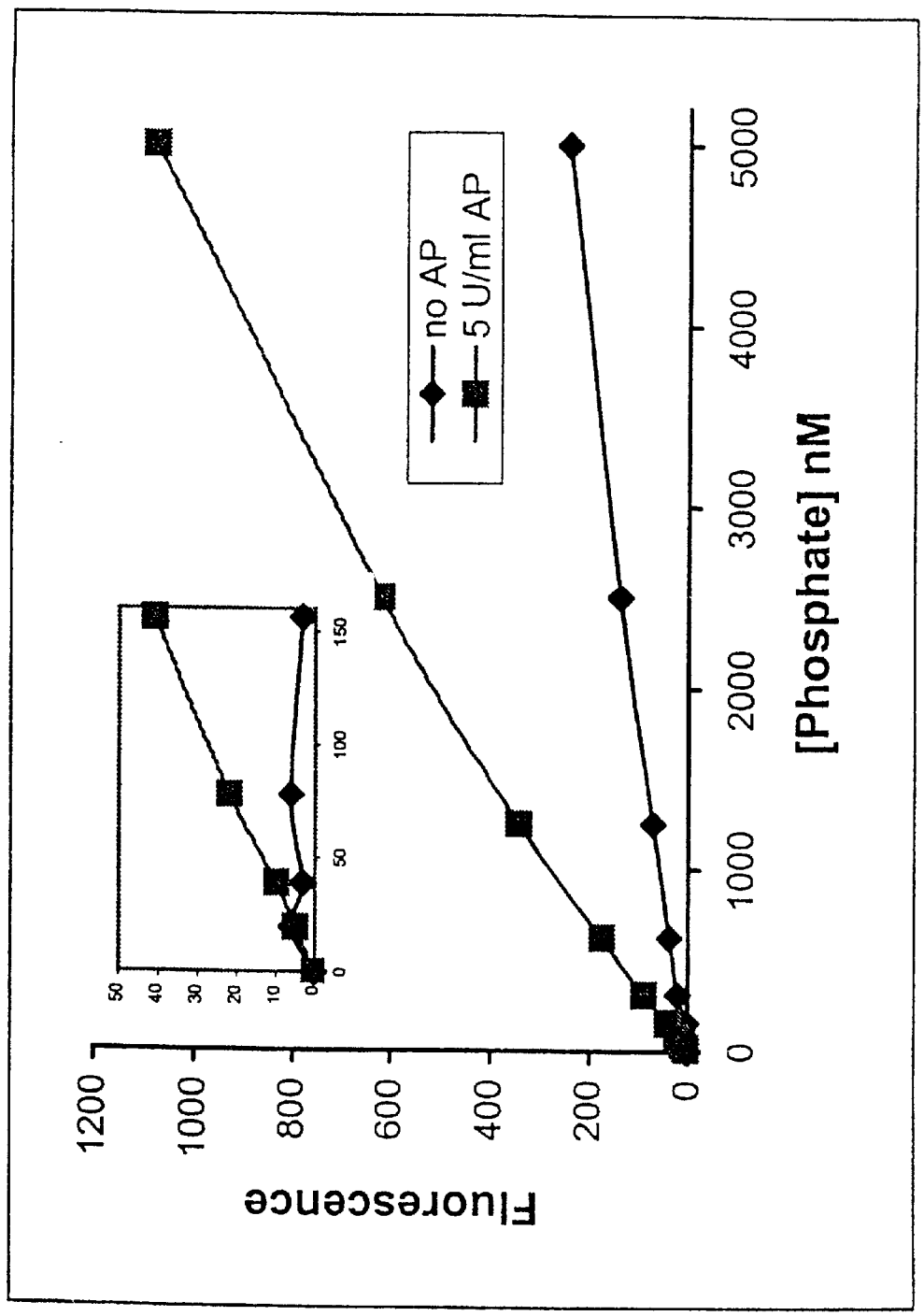
FIG. 1: The presence of alkaline phosphatase enhances the detection of inorganic phosphate in an enzyme system of the present invention, as described in Example 10.

The instant method is highly useful for characterizing a sample, where such characterization includes the detection of the presence or absence of inorganic phosphate in the sample, quantitation of the amount of inorganic phosphate in the sample, detection or quantitation of a phosphate-producing or phosphate-depleting condition or enzyme, or of a substrate for such an enzyme.

The instant invention comprises coupling a phosphate-dependent enzyme reaction with an enzymatic reaction producing hydrogen peroxide, which is itself coupled to a peroxidase enzyme reaction in the presence of a particular chromogenic or fluorogenic peroxidase substrate. Typically, the sample of interest is treated, either simultaneously or sequentially, with a phosphorylase enzyme, a phosphorylase enzyme substrate, an oxidase enzyme, a peroxidase enzyme, and a peroxidase enzyme substrate to produce a reaction mixture. The reaction mixture is incubated under conditions such that when inorganic phosphate is present in the reaction mixture, the phosphorylase enzyme converts the inorganic phosphate and said phosphorylase enzyme substrate into one or more phosphorylase products. The oxidase enzyme is selected so that at least one of the phosphorylase products is a substrate for the oxidase enzyme, such that the oxidase substrate is converted into one or more oxidase products, at least one of which is hydrogen peroxide. Upon the generation of hydrogen peroxide, the peroxidase enzyme converts the peroxidase enzyme substrate into a detectable product.

Appropriate conditions for the method of the instant invention are the conditions necessary for each enzyme system to function are met, include appropriate component concentrations, solution temperature, ionic strength, and incubation time. Such conditions also include the presence of whatever additional substances that are required for each enzyme system, such as any enzyme cofactors that are required, appropriate buffering agents, and any additional substrates required. Such conditions are not necessarily optimal conditions for producing maximal enzymatic activity for any given singular enzyme in the enzyme system. Appropriate incubation conditions for a given enzyme, or coupled enzyme system, are generally known in the art or are readily determined using standard methods known in the art.

The instant method further comprises detecting the presence or amount of the detectable product of the peroxidase enzyme in the reaction mixture, and correlating the presence or amount of the detectable product with the presence or amount of inorganic phosphate in the reaction mixture. Typically, the detectable product is detected calorimetrically or fluorimetrically.

The phosphorylase enzyme and oxidase enzyme of the invention are selected in combination, so that in the presence of inorganic phosphate the two enzymes produce hydrogen peroxide. Any phosphorylase enzyme that produces a product that is a substrate for an oxidase enzyme, is an appropriate phosphorylase enzyme. Any oxidase enzyme that acts upon a product of the selected phosphorylase enzyme to produce hydrogen peroxide ($H_2O_2$) is an appropriate oxidase enzyme. Selected oxidase enzymes initially produce superoxide ion, which then spontaneously dismutates to hydrogen peroxide. This dismutation can be accelerated by the addition of superoxide dismutase, which catalyzes the following dismutation reaction:

$$2O^{2-} + 2H^+ \rightarrow O_2 + H_2O$$

Selected examples of coupled enzyme systems include, but are not limited to, the following coupled enzyme systems.

Maltose Phosphorylase/Glucose Oxidase

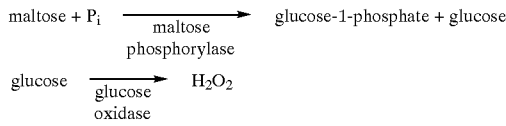

Trehalose Phosphorylase/Glucose Oxidase

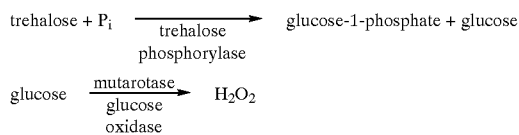

Purine Nucleoside Phosphorylase/Xanthine Oxidase

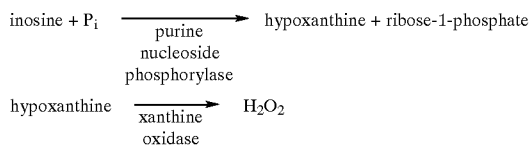

Or, alternatively

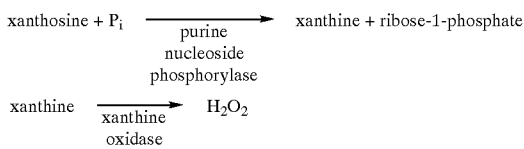

The coupled phosphorylase and oxidase enzyme system is then coupled with a peroxidase enzyme system. Any enzyme that catalyzes the oxidation of the peroxidase enzyme substrate in the presence of hydrogen peroxide is a suitable peroxidase enzyme, including microperoxidases, hemoglobin, and synthetic polymers that possess peroxidase activity. Typically, the peroxidase used is a horseradish peroxidase.

The peroxidase enzyme is optionally free in the reaction mixture, or is optionally immobilized on a substrate, such as a chip or the walls of a microplate well. In another embodiment the instant method utilizes the peroxidase enzyme present in a biological sample itself, such as a naturally occurring cellular peroxidase.

The peroxidase enzyme substrates of the instant method are derivatives of dihydroxanthenes or phenoxazines that are colorless and nonfluorescent until oxidized by the peroxidase enzyme, and have the formula:

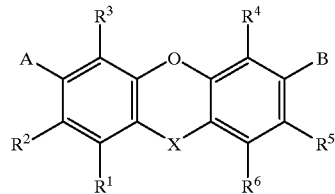

wherein $R^2$, $R^3$, $R^4$ and $R_5$ are independently H, F, Cl, Br, I, CN or $C_1$–$C_6$ alkyl, or $C_1$–$C_6$ alkoxy. Where the substituent is an alkyl or alkoxy, it is optionally further substituted by F, Cl, Br, I, a carboxylic acid, a salt of carboxylic acid, or a carboxylic acid ester of a $C_1$–$C_6$ alcohol, sulfonic acid, or a salt of sulfonic acid. $R^2$–$R^5$ are typically independently H, F, Cl, Br, methoxy or ethoxy. In one embodiment, $R^2$–$R^5$ are independently H, F, or Cl. In another embodiment, $R^2$ and $R^5$ are independently F or Cl. In yet another embodiment, $R^2$ and $R^5$ are F.

Substituents $R^1$ and $R^6$ are typically H. In another embodiment, $R^1$ taken in combination with $R^2$, or $R^5$ taken in combination with $R^6$, or both, form a fused aromatic six membered ring, and each such fused ring is optionally and independently substituted one or more times by F, Cl, Br, I, CN, $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol, sulfonic acid, or a salt of sulfonic acid.

Ring substituents A and B are independently OH or $NR^8R^9$. The nitrogen substituents $R^8$ and $R^9$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl. Where the $R^8$ or $R^9$ substituents are alkyl or contain alkyl, the alkyl portions are optionally substituted by amino, hydroxy, carboxylic acid, a salt of carboxylic acid, or a carboxylic acid ester of a $C_1$–$C_6$ alcohol. In another embodiment, $R^8$ in combination with $R^9$ forms a saturated 5- or 6-membered heterocycle that is a piperidine, a morpholine, a pyrrolidine or a piperazine, which is optionally substituted by methyl, carboxylic acid, a salt of carboxylic acid, a carboxylic acid ester of a $C_1$–$C_6$ alkyl, sulfonic acid, or a salt of sulfonic acid.

In another embodiment of the invention, $R^8$ in combination with an adjacent $R^2$ or $R^5$, or $R_9$ in combination with an adjacent $R^3$ or $R^4$, or a combination thereof, form 5- or 6-membered rings that are saturated or unsaturated. The resulting fused ring is optionally and independently substituted one or more times by F, Cl, Br, I, CN, $C_1$–$C_6$ alkyl, or $C_1$–$C_6$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol, sulfonic acid, or salt of sulfonic acid.

Selected, but not exclusive, structures of peroxidase substrates that incorporate fused 5- or 6-membered rings are provided below (additional substituents are not shown for the sake of clarity).

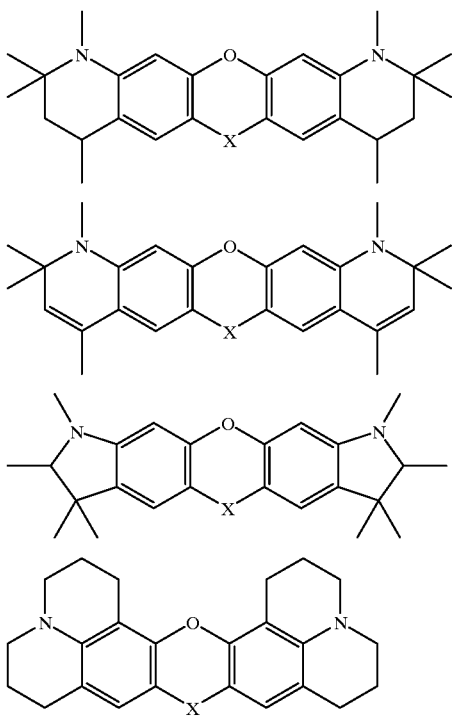

The ring member X is optionally N—(C=Y)—R$^{10}$, N—(SO$_2$)—R$^{11}$, or CHR$^{12}$. Where X is CHR$^{12}$, the resulting peroxidase substrate is a dihydroxanthene. Where X is a substituted nitrogen, the resulting peroxidase substrate is a phenoxazine.

Where X is N—(C=Y)—R$^{10}$, the Y atom is O or S, and R$^{10}$ is hydrogen, C$_1$–C$_6$ alkyl, C$_1$–C$_6$ perfluoroalkyl, C$_1$–C$_6$ alkoxy, C$_1$–C$_6$ alkenyl, aryl, amino, C$_1$–C$_6$ alkylamino, or C$_2$–C$_{12}$ dialkylamino. Typically, Y is O, and R$^{10}$ is alkyl or perfluoroalkyl. In one embodiment, R$^{10}$ is alkyl or perfluoroalkyl having 1–3 carbons.

Where X is N—(SO$_2$)—R$^{11}$, R$^{11}$ is C$_1$–C$_6$ alkyl, C$_1$–C$_6$ perfluoroalkyl, C$_1$–C$_6$ alkenyl, aryl, amino, C$_1$–C$_6$ alkylamino, or C$_2$–C$_{12}$ dialkylamino, the alkyl portions of which have 1–6 carbons. Typically R$^{11}$ is alkyl or perfluoroalkyl. In one embodiment, R$^{11}$ is alkyl or perfluoroalkyl having 1–3 carbons.

Where X is CHR$^{12}$, R$^{12}$ is H, F, CN, a carboxylic acid, a salt of carboxylic acid, or a carboxylic acid ester of a C$_1$–C$_6$ alcohol. In another embodiment, R$^{12}$ is a saturated or unsaturated C$_1$–C$_6$ alkyl that is optionally substituted one or more times by F, Cl, Br, carboxylic acid, a salt of carboxylic acid, a carboxylic acid ester of a C$_1$–C$_6$ alcohol, a sulfonic acid, a salt of sulfonic acid, amino, alkylamino, or dialkylamino, the alkyl groups of which have 1–6 carbons. In yet another embodiment, R$^{12}$ has the formula

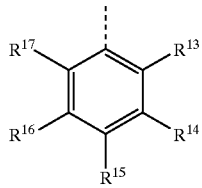

where the substituents R$^{13}$, R$^{14}$, R$^{15}$, R$^{16}$, and R$^{17}$ are independently H, F, Cl, Br, I, sulfonic acid, salt of sulfonic acid, a carboxylic acid, a salt of carboxylic acid. Typically R$^{13}$ is sulfonic acid, salt of sulfonic acid, carboxylic acid or salt of carboxylic acid.

In one aspect of the invention, the peroxidase substrate is a dihydrofluorescein having the formula

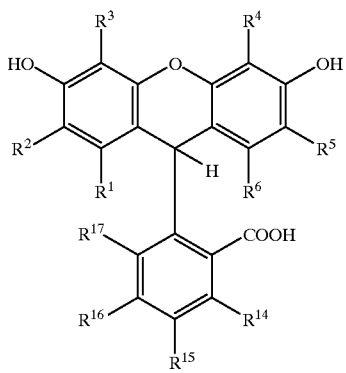

In another aspect of the invention, the peroxidase substrate is a dihydrorhodamine having the formula

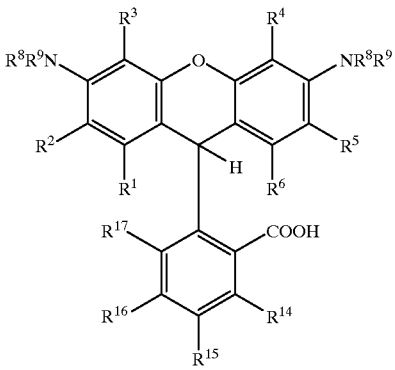

In another aspect of the invention, the peroxidase substrate is a phenoxazine (or dihydroresorufin) having the formula

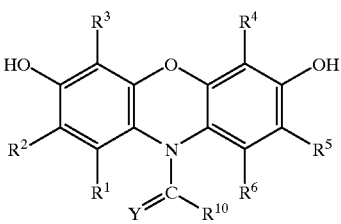

In each aspect of the invention, oxidation of the substrate by the peroxidase enzyme, in the presence of hydrogen peroxide, results in conversion of the essentially colorless substrate to a colored and/or fluorescent species, that is then easily detected or quantified. A variety of useful substrates suitable for the instant method are available from Molecular Probes, Inc., Eugene, Oreg. Particularly suitable substrates include dihydrofluoresceins (also known as fluorescing), dihydrorhodamines, and 10-acetyl-3,7-dihydroxyphenoxazine (sold under the trademark AMPLEX RED).

Analytes

While the method of the invention is primarily useful for the detection and/or quantitation of inorganic phosphate, it is understood that a variety of other analytes may be detected or quantified either by coupling the analyte to the production or depletion of phosphate, or by the detection of analytes that are consumed or produced during the course of the method.

The detection or quantification of a phosphate-producing enzyme in a sample typically comprises performing the instant assay as described above, with the addition of a an appropriate substrate for the phosphate-producing enzyme of interest to the reaction mixture. In the presence of the phosphate-producing enzyme, the phosphate-producing enzyme substrate is converted to products, one of which is inorganic phosphate, which is detected and/or quantitated as described above.

For example, the phosphate-producing enzyme ATPase is assayed in samples suspected to contain the enzyme by the addition of an excess of the substrate ATP to the reaction mixture. The ATPase present in the reaction mixture hydrolyzes the ATP to ADP and P$_i$, that is then detected by the method of the invention. The concentration of P$_i$ produced is then correlated with the amount of ATPase in the original sample. In this type of assay, it is important to either analyze for the amount of $P_1$ and ATP already present in the sample, or to remove interfering $P_1$ as described below. The careful performance of controls for endogenous interferants is optionally included to increase selectivity of the analysis for the proper analyte.

The above assay is readily converted to an assay for ATP by the addition of an excess of ATPase to the reaction mixture, rather than ATP. The amount of $P_1$ produced is then readily correlated with the amount of ATP present in the original sample.

Similarly, the method of the invention is readily modified to assay for the hydrolysis of a sugar phosphate by the enzyme alkaline phosphatase. In this aspect of the invention, the assay is optionally performed continuously at or near neutral pH or in a discontinuous method using alkaline pH followed by acidification to near-neutral pH for the detection of the $P_1$ that is produced. When used in a continuous assay, this method routinely detects as little as 10 pmoles glucose-1-phosphate in a sample.

The method of the invention is also well-suited for the detection of necessary components of the coupled enzyme system by the addition of inorganic phosphate. For example, the maltose phosphorylase/glucose oxidase system is readily adapted for the detection of maltose by the addition of excess phosphate to a sample in combination with a maltose phosphorylase enzyme, a glucose oxidase enzyme, a peroxidase enzyme and an appropriate peroxidase substrate (as described in Example 11 and FIG. 2). Other substrates are assayed using the appropriate phosphorylase/oxidase enzyme system.

A variety of enzymes that produce or consume inorganic phosphate, or that produce pyrophosphate, are known in the art and are readily identified in the scientific literature (see for example ENZYMES, $3^{rd}$ Ed., Dixon et al., pp 684–972, 1979, incorporated by reference). Particular enzymes that may be assayed using the instant method include, but are not limited to, the following:

1,3-β-D-glucan phosphorylase
1,3-β-D-oligoglucan phosphorylase
5'-Nucleotidase
Acetyl-CoA synthetase
Acid phosphatase
Adenosine 5'-diphosphatase
Adenosine deaminase
Adenylyl cyclase
ADP-glucose pyrophosphorylase
Alkaline phosphatase
Aminoacyl-tRNA transferases
Aspartate transcarbamylase
ATPases
cAMP-phosphodiesterase
Casein phosphatase
Cellobiose phosphorylase
Cellodextrin phosphorylase
cGMP phosphodiesterase
Cob(I)alamim adenosyltransferase
Creatine kinase
Dethiobiotin synthetase
Dihydropteroate synthase
Dimethylallyltransferase
DNA polymerase
Enoylpyruvate transferase
Farnesyltransferase
Geranyltransferase
Glyceraldehyde-3-dehydrogenase
Glycerol kinase
Glycogen phosphorylase
GTPases
Guanylate cyclase
$IP_3$ phosphatase
Laminaribiose phosphorylase
Maltose phosphorylase
Methionine adenosyltransferase
myo-inositol monophosphatase
myo-inositol synthase
PC-PLC
Phosphodiesterases
Phosphohistidine phosphatase
Phospholysine phosphatase
Phosphorylases
Phosphorylase a
Phosphorylase a phosphatase
Phosphorylase b
Phosphorylase kinase
Prenyl transferase
Presqualence synthase
Protein serine/threonine phosphatase
Protein tyrosine phosphatase
Purine-nucleoside phosphorylase
Pyrophosphatase
Pyruvate oxidase
RNA polymerase
Rubber allyltransferase
Sphingomyelinase
Sucrose phosphorylase
Terpernoid-allyltransferase
Thiaminphosphate pyrophosphorylase
α,α-Trehalose phosphorylase
Xanthine phosphoribosyltransferase Particular analytes that may be assayed using the instant method include, but are not limited to, the following:

ATP
ADP
AMP
cAMP
Adenosine
Creatine phosphate
Maltose
Glucose-1-P (and other sugar phosphates)
Glycogen
GTP, cGMP
Inosine
$IP_3$
myo-inositol monophosphate
Pyrophosphate The use of the method of the instant invention to assay for enzymes or other analytes in phosphate-dependent systems is demonstrated by the following assays.

Assay of $Na^+,K^+$-ATPase

The sodium/potassium pump is a cation exchanger found in the plasma membrane of all mammalian cells. It functions to expel 3 sodium ions from the cell for 2 potassium ions into the cell, thereby creating an electrochemical gradient across the cell membrane. ATP is hydrolyzed to ADP and $P_1$ by the enzyme $Na^+,K^+$-ATPase, which serves as the energy source to drive the pump. Alterations in the activity of this enzyme are associated with some forms of hypertension and chronic renal failure. The production of $P_1$ is monitored directly by the method of the instant invention, thereby permitting a convenient assay for $Na^+,K^+$-ATPase (Example 3).

Assay of 5'-Nucleotidase

This phosphohydrolase is a common marker for plasma membranes. 5'-Nucleotidase converts 5'-nucleotides to their corresponding nucleoside and $P_i$. The activity of this enzyme is increased in certain forms of liver disease, and particularly with hepatic carcinoma. 5'-Nucleotidase is readily assayed using the method of the instant invention (Example 4).

Assay of Protein Tyrosine Phosphatase

The protein tyrosine phosphatases remove phosphate from the tyrosine residues of specific protein substrates. This family of enzymes is important in regulating signal transduction cascades, and has been implicated in the heterologous desensitization of G-protein coupled receptors. Alterations in the activity of protein tyrosine phosphatases (specifically PTP-1B) have been linked to diabetes, insulin resistance and obesity. Protein tyrosine phosphatase is readily assayed using the method of the instant invention (Example 5).

Protein Serine/Threonine Phosphatase

The protein serine/threonine phosphatases remove phosphate from serine or threonine residues of specific protein substrates. This family of enzymes is involved with multiple signaling pathways. Alterations in the activity of specific serine/threonine phosphatases are potentially involved with a variety of disease states including Alzheimer and Hodgkin's diseases. Protein serine/threonine phosphatase is readily assayed using the method of the instant invention (Example 6).

Apyrase

Apyrase (ATP diphosphohydrolase) is an enzyme found in high levels in the vasculature that hydrolyzes both ATP and ADP to AMP. The activity of this enzyme is critical for inhibition of platelet aggregation. A loss in apyrase activity in reperfusion injury has been observed, and the administration of apyrases to experimental animals has been shown to improve xenograft survival. Apyrase is readily assayed using the method of the instant invention (Example 7).

Adenylyl Cyclase and Pyrophosphatase

Adenylyl cyclase is an enzyme whose activity is linked to transmembrane receptors via stimulatory G-proteins ($G_s$). Upon receptor binding and G-protein activation, adenylyl cyclase is stimulated to convert ATP to the cyclic nucleotide second messenger, cAMP and pyrophosphate ($PP_i$). cAMP evokes a variety of signaling events by its activation of cAMP-dependent protein kinase (PKA) including vasorelaxation. Alterations in adenylyl cyclase activity may be involved in the pathology of a variety of diseases by its involvement in complex signaling cascades. It is thought to play a role in the loss of $\beta$-adrenergic responsiveness associated with aging. Adenylyl cyclase and pyrophosphatase are readily assayed using the method of the instant invention (Example 8).

Prenyl Transferase and Pyrophosphatase

Similar to the above, the nucleophilic reaction of a thiol with farnesyl pyrophosphate, catalyzed by farnesyl transferase, results in liberation of inorganic pyrophosphate, which in turn is converted to $P_1$ by the addition of pyrophosphatase. A variety of prenyl transferases are readily assayed using the method of the instant invention, including farnesyl transferase, geranyl transferase, and geranylgeranyl transferase.

Detection of Phosphate Contamination of Reagents and Other Samples

Because phosphate is a ubiquitous component of biological systems, many research materials of biological origin are contaminated with trace amounts of phosphate. This is particularly true for isolated enzymes or other proteins. The instant method is readily adapted to the detection and quantification of phosphate contaminants in a variety of substances (Example 9). Phosphate contaminants are then readily removed, for example by using the pretreatments described below.

Sensitivity Enhancement

The sensitivity of the instant method is optionally enhanced by adding to the reaction mixture an enzyme capable of converting a side product of the coupled enzyme system into either an additional equivalent of substrate for a previous enzymatic conversion (substrate recycling), or an additional equivalent of a substrate for a subsequent enzymatic conversion (signal amplification).

By "side product" is meant any product of an enzymatic reaction that is not directly required for a subsequent coupled enzymatic reaction. For example, in the purine nucleoside phosphorylase/xanthine oxidase enzyme system, xanthine oxidase converts hypoxanthine into uric acid and hydrogen peroxide. The uric acid thereby produced is a side product with respect to the PNP/xanthine oxidase system. The addition of the enzyme uricase (urate oxidase) to the reaction mixture catalyzes the oxidation of uric acid and the production of an additional equivalent of hydrogen peroxide, thereby increasing the amount of detectable product formed by the action of the peroxidase enzyme.

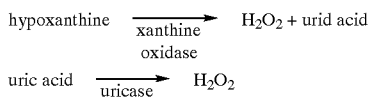

Substrate recycling typically refers to the enzymatic conversion of a side product of the phosphorylase enzyme into a substrate for the phosphorylase enzyme. In one aspect of the invention, the phosphorylated product of the phosphorylase enzyme is dephosphorylated, producing an additional equivalent of inorganic phosphate, which is utilized by the phosphorylase enzyme to turn over additional phosphorylase substrate. This method of substrate recycling effectively increases the amount of detected inorganic phosphate in the reaction mixture.

For example, in the purine nucleoside phosphorylase/xanthine oxidase system the addition of alkaline phosphatase to the reaction mixture results in the conversion of a side product, ribose-1-phosphate, to ribose and $P_i$, which is then taken up by the purine nucleoside phosphorylase. The addition of an appropriate phosphatase enzyme may generally be utilized to enhance the sensitivity of the instant method, as in the case of the maltose phosphorylase/glucose oxidase enzyme system (Example 10 and FIG. 1).

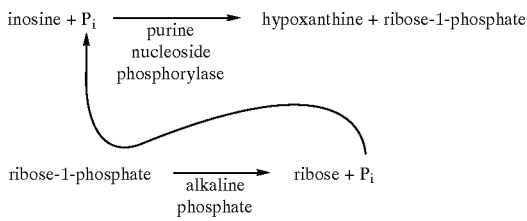

Both the strategy of signal amplification and substrate recycling requires that the side products used are not substrates for other enzymes present in the reaction mixture. The use of appropriate enzyme inhibitors for such other enzymes may be used to suppress the activity of undesired other enzymes.

Pretreatment of Samples and Reagents

The instant method for detecting phosphate is highly sensitive. The assay is therefore susceptible to trace quantities of contaminating phosphate or peroxide which elevate the background signal and therefore decrease the sensitivity of the assay. It is therefore preferable to remove such contaminants from the necessary reagents and buffers, and optionally the sample itself, before proceeding with the analysis.

Contaminating peroxide is readily removed by the use of a catalase enzyme. Catalase enzymes catalyze the following reaction:

$$2H_2O_2 \rightarrow 2H_2O + O_2$$

Catalase represents an efficient method of removing trace hydrogen peroxide from samples, buffers and reagents. The sample of interest is treated with a catalase enzyme, and the catalase enzyme is then removed (for example, by chromatography on SEPHAROSE resin or SEPHADEX resin). In a particularly useful aspect of the invention, the sample is exposed to a catalase enzyme that is immobilized on a substrate or matrix, thereby greatly simplifying removal of the catalase from the reaction system. The immobilized catalase is typically removed by sedimentation, filtration, centrifugation, or any other means suitable to removing the immobilized enzyme. In a particular embodiment of the invention, the catalase enzyme is bound to agarose, or another substrate that permits the reagent or sample to flow past the immobilized enzyme. Such a flow-by system has particular utility for automated assays, such as for high-throughput screening.

In another aspect of the invention, one or more reagents or enzymes is purified prior to use in the instant method. Trace peroxide is removed from the assay components using catalase, and trace phosphate is removed by use of one of the phosphorylase enzymes, for instance by using a combination of maltose and maltose phosphorylase. Where the assay utilizes the production of glucose (as in the maltose phosphorylase/glucose oxidase enzyme system), trace glucose is removed from assay components by pretreatment with glucose oxidase.

In one aspect of the invention, the assay utilizes the maltose phosphorylase/glucose oxidase enzyme system, wherein the maltose used is treated with a glucose oxidase enzyme and a catalase enzyme to remove contaminating glucose and peroxides, and the sample of interest is treated with a combination of a maltose phosphorylase enzyme, a glucose oxidase enzyme, and a catalase enzyme to remove contaminating phosphate, glucose and peroxide. Preferably, this pretreatment is accomplished in a single step. In a particular embodiment of the invention, one or more enzymes used to pretreat samples or reagents are immobilized on a polymeric microparticle, permitting the pretreatment enzymes to be easily removed from the sample prior to performing the assay.

In another aspect of the invention, the instant method is utilized to detect and/or quantify a phosphate-producing enzyme. In this embodiment, the sample is purified by treatment with the a phosphorylase enzyme, an oxidase enzyme, and a peroxidase enzyme in the absence of the peroxidase enzyme substrate. Any phosphate present in the sample is converted to hydrogen peroxide, which is then removed by treatment with a catalase enzyme, as described above. The catalase enzyme is then separated from the phosphate-free sample, and the addition of the peroxidase enzyme substrate permits detection and/or quantification of newly produced phosphate, and thereby the presence or activity of the phosphate-producing enzyme.

Method of Use

The assay of the invention typically comprises treating a sample of interest with the appropriate enzymes and reagents such that the presence of the analyte of interest results in the appearance of color and/or fluorescence. If the color or fluorescence is detected during the course of the enzymatic reaction, the assay is a continuous assay. Rapid testing for the presence and activity of the target analyte is provided by the appearance of product color or fluorescence.

The sample is typically an aqueous or aqueous miscible solution that is obtained directly from a liquid source, or is an aqueous suspension of a solid or semi-solid material, or is an aqueous wash from a solid or semi-solid material that is known or suspected to contain inorganic phosphate, or another analyte as described above. The sample is optionally obtained from an environmental source such as soil, water, or air, including those from an industrial source, such as taken from a waste stream, a water source, a supply line, or a production lot. Industrial sources also include fermentation media, such as from a biological reactor or food fermentation process. Industrial sources alternatively include chemical reactors and bioreactors. Alternatively, the sample comprises fluids that are cell lysates of blood cells, cultured cells, muscle tissue, neurons and the like; extracellular fluids in areas immediately outside of cells; in vesicles; in vascular tissue of plants and animals; or are biological fluids such as blood, saliva, and urine. In a particular aspect of the invention, the sample is a cell lysate. In another aspect of the invention, the sample is a water sample. The sample is optionally clarified before use, such as by filtration or centrifugation.

Either an aliquot of the sample of interest, or optionally the entire sample is combined with the necessary enzymes and substrates to form the reaction mixture. The enzymes used to practice the invention are optionally free in solution, or are immobilized in or on a solid or semi-solid material or a membrane such as in an agar matrix or on a nylon membrane. Incorporation of the enzymes in a matrix such as agar can be used to detect, for instance, generation of phosphate or analyte enzymes by cells grown in the matrix. The sample is typically added in the form of a solution but can also be immobilized on a carrier such as a natural or synthetic polymer or in a matrix such as agar.

The sample of interest is combined with the enzymes of interest under necessary and sufficient conditions to allow the coupled enzymatic reactions to occur. Necessary and sufficient conditions for enzymatic reaction are any conditions that permit the enzymatic reaction to proceed to yield at least the minimum detectable optical response. These conditions may be affected by temperature, pH and changes in composition of the medium. Most enzymes are functional at physiological temperature and pH, but may be affected by the presence or absence of co-factors or inhibitors and other features widely recognized by enzymologists. Suitable conditions for one enzyme may be unsuitable conditions for a different enzyme. Conditions of the enzymatic reaction can typically be adjusted to accelerate or decelerate the enzymatic reaction or to favor or hinder an enzymatic reaction. Necessary and sufficient conditions for a given combination of enzymes used in the instant method assay are readily determined using methods well-known in the art.

The sample is incubated with the reaction mixture for a period of time necessary to allow the coupled enzymatic reactions to occur. The incubation period needed for an enzyme substrate is the amount of time required to determine the presence or absence of inorganic phosphate or other analyte of interest. Under the most favorable conditions this time is less than one hour and may be as short as seconds, up to 10 minutes. The results are typically monitored continuously over a period of time. Alternatively the results are monitored by intermittent sampling of the reaction mixture.

The sensitivity of the instant method permits the assays described herein to be performed in reaction mixtures of small volume. This is particularly useful for methods generally known as high-throughput screening. In one embodiment, the reaction mixture is present in the well of a microplate. In another embodiment, the reaction mixture is present on a microfluidic chip. In one aspect of the invention, the reaction mixture has a volume of less than or equal to 200 microliters.

To detect the appearance of the detectable product, the reaction mixture is illuminated at a wavelength that results in a detectable optical response. A detectable optical response means a change in, or occurrence of, an optical signal that is detectable either by observation or instrumentally. Where the assay is a colorimetric assay, the detectable response is typically the appearance of, or increase in, color in the reaction mixture. Where the assay is a fluorometric assay, the detectable response is typically the appearance of, or increase in, fluorescence emission. The degree and/or location of color and/or fluorescence, compared with a standard or expected response, indicates whether and to what degree the sample possesses a given characteristic. Typically, the amount of product dye present is determined by measuring the intensity of the colorimetric absorbance or fluorescence emission.

Where the appearance of product dye is detected by fluorescence, the excitation wavelength of the illumination preferably occurs at greater than 480 nm, more preferably at greater than 530 nm, and most preferably at about 570 nm. In one aspect of the invention, the resulting fluorescence emission occurs at greater than 500 nm, more preferably at greater than 550 nm, and most preferably at about 585 nm.

Equipment that is useful for illuminating the reaction mixture includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

The progress of the assay is typically measured by comparing the detectable optical response to a standard curve generated with known amounts of the analyte of interest, according to methods known in the art (see Example 1).

Kits

In another aspect of the invention, the reagents and enzymes necessary for carrying out the method of the invention are packaged as a kit. The kit may be commercially utilized for the detection or quantitation of phosphate, or of a phosphate-producing or phosphate-consuming enzyme, or other phosphate-dependent condition, as described above.

The kits of the invention typically comprise a suitable phosphorylase enzyme, a suitable oxidase enzyme, a suitable peroxidase enzyme, and a peroxidase enzyme substrate, as described above. The kits optionally further comprise inorganic phosphate for use as a calibration standard. In another embodiment, the kit further comprises the product dye corresponding to the peroxidase enzyme substrate for use as a standard. The kit optionally further comprises a phosphate-dependent enzyme, such as a pyrophosphatase enzyme, for use in a coupled enzymatic reaction.

In one aspect of the invention, the kit comprises a purine nucleoside phosphorylase, a xanthine oxidase, a horseradish peroxidase, and AMPLEX RED reagent, and optionally further comprises inosine or xanthosine. In another aspect of the invention, the kit comprises a maltose phosphorylase, a glucose oxidase, a horseradish peroxidase, and AMPLEX RED reagent, and optionally comprises maltose that is essentially glucose-free.

The examples below are given so as to illustrate the practice of this invention. They are not intended to limit or define the entire scope of this invention.

EXAMPLES

Example 1

Assay for Inorganic Phosphate ($P_i$) Using Purine Nucleoside Phosohorylase and Xanthine Oxidase A phosphate standard curve is prepared by diluting 100 mM phosphate ion in 0.50 mM Tris buffer (pH 7.5) to produce phosphate concentrations of 0–100 $\mu$M in a 96-well microplate. Buffer with no added phosphate is used as a negative control. The phosphate-containing samples of interest and phosphate controls in 0.50 mM Tris buffer are diluted into separate wells of the microplate.

A working solution of 100 $\mu$M AMPLEX RED reagent, 1.0 U/mL superoxide dismutase, 0.4 U/mL horseradish peroxidase, 1 U/mL nucleoside phosphorylase, 0.05 U/mL xanthine oxidase, and 200 $\mu$M inosine is prepared in 100 mM Tris-HCl, pH 7.5. The reaction is initiated by adding 50 $\mu$L of the working solution to each microplate well containing either samples or phosphate controls. The microplate is incubated for 30 minutes or longer at 37° C., protected from light. The fluorescence of the microplate wells is measured using a fluorescence microplate reader equipped with ~530 nm excitation and ~590 emission filters. The fluorescence is measured at multiple time points to follow the kinetics of the reaction. The background fluorescence for each point is corrected by subtracting the fluorescence measured for controls having no phosphate. The assay is capable of detecting phosphate concentrations as low as ~20 nM, with a linear response up to ~10 $\mu$M.

The fluorogenic peroxidase substrate dihydrorhodamine 123 (Molecular Probes, Inc., Eugene, Oreg.) can also be used to assay for $P_i$ by substituting an equal concentration of dihydrorhodamine 123 for AMPLEX RED reagent in the assay above. The sensitivity of the assay using either reagent is about the same (~20 nM $P_i$); however, the intrinsic background fluorescence of the dihydrorhodamine 123 results in a reduced linear range of the assay to <1 μM $P_i$.

Example 2

Assay for Inorganic Phosphate ($P_i$) Using Maltose Phosphorylase and Glucose Oxidase The assay procedure is as given above, excepting that the working solution contains 50 μM AMPLEX RED reagent, 1 U/mL horseradish peroxidase, 1 U/mL glucose oxidase, 2 U/mL maltose phosphorylase, and 200 μM maltose in 50 mM Tris-HCl, pH 7.2.

The microplate is incubated for 60 minutes at 37° C., protected from light. The fluorescence of the microplate wells is measured using a fluorescence microplate reader equipped with ~530 nm excitation and ~590 emission filters. The assay can detect phosphate concentrations as low as ~200 nM.

Example 3

Assay for $Na^+,K^+$-ATPase $Na^+,K^+$-ATPase is assayed in 100 mM Tris-HCl, pH 7.5 buffer containing 150 mM NaCl, 20 mM KCl, 5 mM $MgCl_2$ and 0.1 mM EDTA. The assay is performed at 37° C. in a 96-well microplate with a 100 μL final volume containing 100 μM inosine, 0.5 U/mL purine nucleoside phosphorylase, 0.025 U/mL xanthine oxidase, 0.5 U/mL superoxide dismutase, 0.2 U/mL peroxidase, 200 μM ATP, and 50 μM AMPLEX RED reagent. After incubation for 30 minutes, the fluorescence is measured with a microplate reader equipped with a 530 nm excitation/590 nm emission filter set. Alternatively, enzymatic activity can be continuously measured. Enzymatic activity can also be measured by absorption changes at about 570 nm, but with somewhat decreased sensitivity. The assay can be performed at any temperature at which the enzymes are active but preferably near room temperature or at 37° C. The effects of variations in the pH and composition of the buffers, enzyme concentrations, reaction times and other variables on the production of the detectable product are easily evaluated by means well known in the art. This general assay method also permits the testing of alternative fluorogenic or chromogenic substrates, as described in the specifications. The high sensitivity of the assay permits reduction of the volume for use in microplates that have greater numbers of wells or use with other detection equipment.

This method detects as little as 0.01 mU/mL of purified $Na^+,K^+$-ATPase with a 30 minute incubation. Even greater sensitivity is obtained following longer incubations. The linear range of the assay is from approximately 0–2.5 mU $Na^+,K^+$-ATPase/mL. Ouabain (a specific $Na^+,K^+$-ATPase inhibitor) at 5 mM inhibits >95% of this enzymatic activity. The assay can also be used to detect ATPase activity in tissue homogenates and cell lysates. For instance, using Sprague-Dawley rat brain, the assay is able to detect ATPase activity from homogenate containing less than 0.5 μg total protein.

The assay is readily modified for the fluorometric measurement of a wide variety of nucleotide triphosphatases, including ATPases (with the addition of ATP) and GTPases (with the addition of GTP).

Example 4

Assay for 5'-Nucleotidase

5'-Nucleotidase is assayed in 100 mM Tris-HCl, pH 7.5 buffer at 37° C. in a 96-well microplate with a 100 μL final volume. Each well contains 100 μM inosine, 0.5 U/mL purine nucleoside phosphorylase, 0.025 U/mL xanthine oxidase, 0.5 U/mL superoxide dismutase, 0.2 U/mL peroxidase, 1 mM $MnCl_2$, 100 μM AMP and 50 μM AMPLEX RED reagent. After 30 minutes the fluorescence is measured with a microplate reader equipped with a 530 nm excitation/590 nm emission filter set. Using the purified enzyme, this method can detect as little as 0.1 mU/mL of 5'-nucleotidase with a linear range from 0 to approximately 25 mU 5'-nucleotidase/mL. levamisole (100 μM) and concanavalin A (2 mg/mL) each inhibit 5'-nucleotidase activity by >80%. The assay can also be used to detect 5'-nucleotidase activity in cell lysates, serum, and intact cells. When using intact HeLa cells, this assay can detect the 5'-nucleotidase activity from fewer than 200 cells.

By proper selection of inhibitors and using the proper controls, it is possible to analyze multiple enzymes from samples such as cell lysates in a single microplate. For example, by adding specific substrates (ATP or AMP for $Na^+,K^+$-ATPase and 5'-nucleotidase, respectively) and specific inhibitors (ouabain or levamisole for $Na^+,K^+$-ATPase and 5'-nucleotidase, respectively) into separate wells of a microplate, and then adding the cell lysate and all other reagent components to each well, it is possible to measure more than one enzyme activity simultaneously on a single sample.

Example 5

Assay for Protein Tyrosine Phosphatase

Protein tyrosine phosphatase activity is assayed in 60 mM MES, pH 6.1 buffer containing 1 mM EDTA. The assay is performed in 96-well microplates using a 25 μL volume. The samples are incubated for 1 hour at 37° C. in the presence of a 50 μM phosphopeptide substrate. The reaction is terminated by addition of 75 μL of 100 mM Tris-HCl, pH 8.0 buffer containing 100 μM inosine, 0.5 U/mL purine nucleoside phosphorylase, 0.025 U/mL xanthine oxidase, 0.5 U/mL superoxide dismutase, 0.2 U/mL peroxidase and 50 μM AMPLEX RED reagent. After incubation for 20 minutes, the fluorescence is measured with a microplate reader equipped with a 530 nm excitation/590 nm emission ifilter set.

Using purified enzyme, this method can detect as little as 30 mU/mL of protein tyrosine phosphatase. The assay can also be used to measure protein tyrosine phosphatase activity in cell lysates and tissue homogenates. When using Jurkat cell lysate, this method can detect protein tyrosine phosphatase activity in less than 5 μg total protein. The activity of this enzyme can be specifically inhibited with 10 μM suramin.

Example 6

Assay for Protein Serine/Threonine Phosphatase

Protein phosphatase 2A (PP-2A) is measured in 100 mM Tris-HCl, pH 7.5 buffer containing 10 μg/mL protamine-HCl, 200 μM NaCl, 5 mM caffeine and 1 mM $MnCl_2$. The assay is performed in 96-well microplates at 37° C. with 100 μL final volume. The final reaction mixture contains 100 μM inosine, 0.5 U/mL purine nucleoside phosphorylase, 0.025 U/mL xanthine oxidase, 0.5 U/mL superoxide dismutase, 0.2 U/mL peroxidase, 50 μM AMPLEX RED reagent and 10 μM phosphorylase-a as a phospho-substrate. The fluorescence is measured after a 30 minute incubation with a microplate reader equipped with a 530 nm excitation/590 nm emission filter set. Protein phosphatase 2B (PP-2B) is similarly measured except using 50 mM imidazole, pH 7.2 buffer containing 1 mM $MnCl_2$, 10 mM $MgCl_2$, 0.4 mM $CaCl_2$, and 5 U/mL calmodulin. This enzyme also uses a specific phosphopeptide substrate (20 $\mu$M final) instead of phosphorylase-a.

Using purified enzyme, these methods can detect as little as 20 mU/mL of either PP-2A or PP-2B. These assays can also be used to measure PP-2A and PP-2B activity in cell lysates or tissue homogenates. Using Sprague-Dawley rat brain homogenate, this method can detect PP-2B activity in less than 5 $\mu$g total protein. Cyclosporin A can be used as a specific inhibitor for this enzyme.

Example 7

Assay for Apyrase

Apyrase activity is measured in 100 mM Tris-HCl, pH 7.5 buffer. The assay is performed in 96-well microplates at 37° C. with a 100 $\mu$L final volume. The final reaction mixture contains 100 $\mu$M inosine, 0.5 U/mL purine nucleoside phosphorylase, 0.025 U/mL xanthine oxidase, 0.5 U/mL superoxide dismutase, 0.2 U/mL peroxidase, 200 $\mu$M ATP and 50 $\mu$M AMPLEX RED reagent. Following a 30 minute incubation, the fluorescence is measured with a microplate reader equipped with a 530 nm excitation/590 nm emission filter set. Using purified enzyme, this method can detect as little as 0.1 mU/mL of apyrase activity. The linear range of the assay is approximately 0–100 mU apyrase/mL. This assay can also be used to measure apyrase activity in endothelial cell lysates and homogenates from vascular tissue.

Example 8

Assay for Adenylyl Cyclase and Pyrophosphatase

Adenylyl cyclase activity is measured using 100 mM Tris-HCl, pH 7.5 buffer. The assay is performed in 96-well microplates at 37° C. with a 100 $\mu$L final volume. The final reaction mixture contains 100 $\mu$M inosine, 0.5 U/mL purine nucleoside phosphorylase, 0.025 U/mL xanthine oxidase, 0.5 U/mL superoxide dismutase, 0.2 U/mL peroxidase, 200 $\mu$M ATP, 0.05 U/mL pyrophosphatase, 1 mM $MgCl_2$ and 50 $\mu$M AMPLEX RED reagent. The fluorescence is measured after a 30 minute incubation with a microplate reader equipped with a 530 nm excitation/590 nm emission filter set. Using purified enzyme, this method can detect as little as 5 mU/mL of unstimulated adenylyl cyclase activity. This assay can also be used to measure adenylyl cyclase activity in cell lysates and tissue homogenates and stimulation of adenylyl cyclase activity by exogenous reagents.

The assay is also used to measure the concentration of cAMP in samples by omission of pyrophosphatase and the inclusion of 3',5'-cyclic nucleotide phosphodiesterase, $Ca^{2+}$, calmodulin and 5'-nucleotidase and allowing the reactions to go to completion, then equating the amount of $P_1$ detected to the amount of cAMP in the original sample. The sensitivity and linearity of this fluorometric assay for cAMP is about 200 nM.

Similar assays that utilize pyrophosphatase to convert pyrophosphate to $P_1$ permit measurement of other pyrophosphate-producing enzymatic reactions such as from nucleic acid polymerases, including during PCR and related procedures. By use of excess pyrophosphate, the assay can be used to assay for pyrophosphatase in samples suspected of containing that enzyme.

Example 9

Detection of Phosphate Contamination of Reagents and Other Samples

Using a combination of reagents such as 100 $\mu$M inosine, 0.5 U/mL purine nucleoside phosphorylase, 0.025 U/mL xanthine oxidase, 0.5 U/mL superoxide dismutase, 0.2 U/mL peroxidase and 50 $\mu$M AMPLEX RED reagent, the $P_1$ concentration of a wide variety of samples, including environmental samples, cell lysates, tissue homogenates, culture media, bodily fluids, chromatographic fractions, etc. can be assayed. For instance it is determined that certain lots of the following reagents purchased from Sigma (St. Louis, Mo.) have the following $P_1$ contaminations: ATP (0.28%), cocarboxylase (1.5%), $Na^+,K^+$-ATPase (0.13 pmol $P_i$/mg protein) and glucose oxidase (0.25 pmol Pi/mg protein).

Example 10

Substrate Recycling

The phosphate assay of Example 2 may be enhanced by the addition of 5 U/mL of alkaline phosphatase in the reaction mixture. The alkaline phosphatase converts the glucose-1-phosphate produced by the maltose phosphorylase to glucose and free phosphate. The glucose produced is then a substrate for the glucose oxidase present in the enzyme system, while the phosphate is utilized by the phosphorylase to produce additional glucose and glucose-1-phosphate.

The addition of alkaline phosphatase results in a ~5-fold increase in sensitivity in the assay, as shown in FIG. 1.

Example 11

Detection of Maltose

The assay for detection and quantitation of maltose utilizes a working solution as described in Example 2, excepting that the solution contains 100 $\mu$M phosphate ion in place of 200 $\mu$M maltose. Instead of a phosphate standard curve, a maltose standard curve is prepared by serial dilution. Solutions having maltose concentrations of 0–50 $\mu$M are used, with buffer with no added maltose as a negative control. The assay is performed on a 96-well microplate as described in Example 1.

Figure 2:
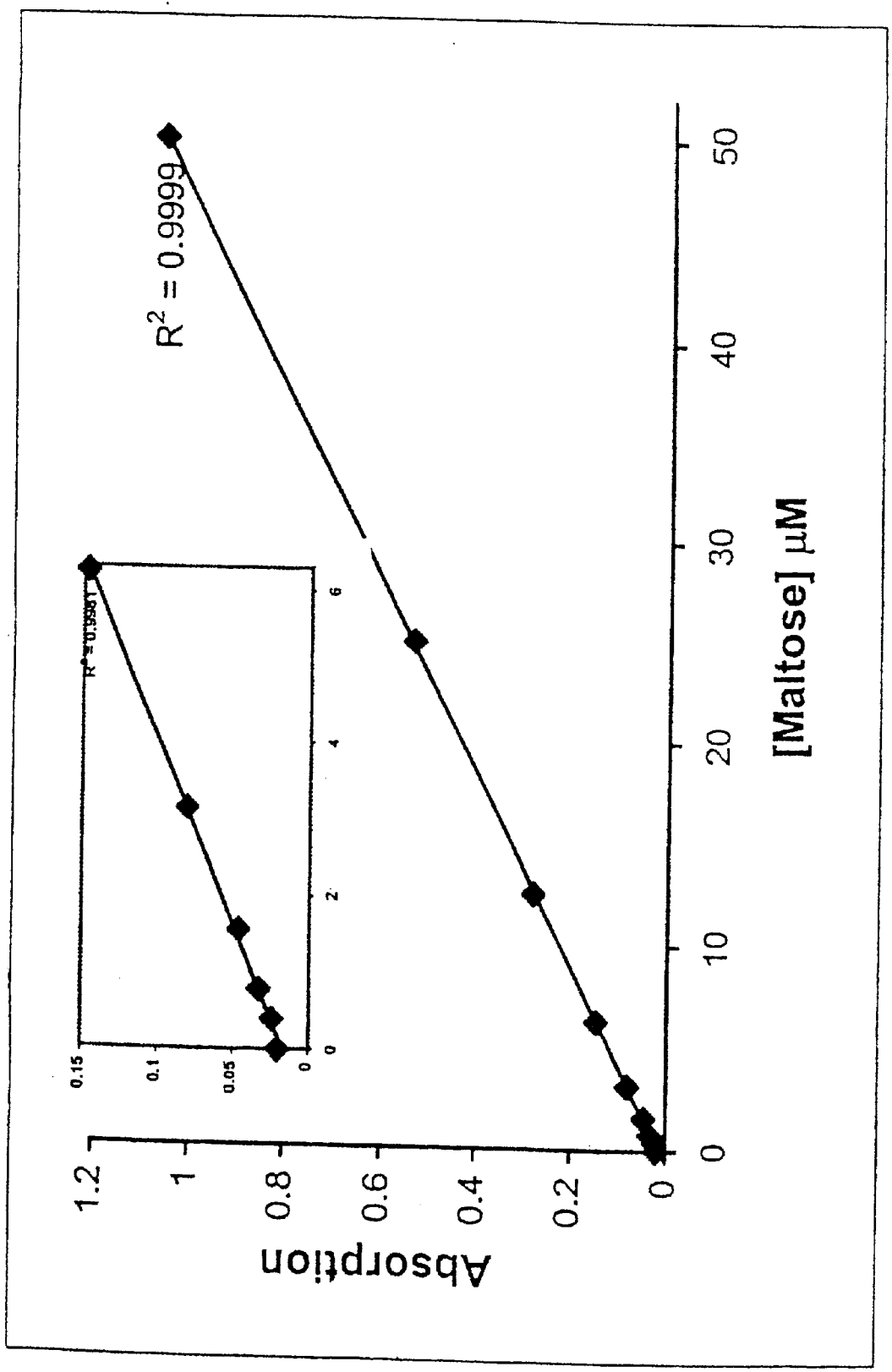
FIG. 2: The detection of maltose using the coupled enzyme system of the invention, as described in Example 11.

The resulting assay is highly linear over the entire range of 0–50 $\mu$M maltose, and is can detect less than 1 $\mu$M maltose, as shown in FIG. 2.

It is to be understood that, while the foregoing invention has been described in detail by way of illustration and example, numerous modifications, substitutions, and alterations are possible without departing from the spirit and scope of the invention as described in the following claims.

What is claimed is:

1. An assay for inorganic phosphate, comprising:
   a) producing a reaction mixture by treating a sample, simultaneously or sequentially, with a phosphorylase enzyme, a phosphorylase enzyme substrate, an oxidase enzyme, a peroxidase enzyme, and a peroxidase enzyme substrate, under conditions such that:
      when inorganic phosphate is present in said reaction mixture, said phosphorylase enzyme converts said inorganic phosphate and said phosphorylase enzyme substrate into one or more phosphorylase products, at least one of which is an oxidase substrate for said oxidase enzyme;

said oxidase enzyme converts said oxidase substrate into one or more oxidase products, at least one of which is hydrogen peroxide;
in the presence of hydrogen peroxide, said peroxidase enzyme converts said peroxidase enzyme substrate into a detectable product;

b) detecting the presence or amount of said detectable product in said reaction mixture; and c) correlating the presence or amount of said detectable product in said reaction mixture with the presence or amount of inorganic phosphate in said reaction mixture;

wherein said peroxidase enzyme substrate has the formula

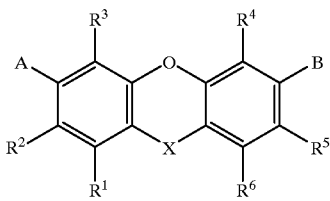

wherein
$R^2$, $R^3$, $R^4$ and $R^5$ are independently H, F, Cl, Br, I, CN; or $C_1$–$C_6$ alkyl, or $C_1$–$C_6$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol, sulfonic acid, or a salt of sulfonic acid;

$R^1$ and $R^6$ are H; or $R^1$ taken in combination with $R^2$, or $R^5$ taken in combination with $R^6$, or both, form a fused aromatic six membered ring that is optionally and independently substituted one or more times by F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol, sulfonic acid, or a salt of sulfonic acid;

A and B are independently OH or $NR^8R^9$, wherein each $R^8$ and $R^9$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alcohol; or $R^8$ in combination with $R^9$ forms a saturated 5- or 6-membered heterocycle that is a piperidine, a morpholine, a pyrrolidine or a piperazine, each of which is optionally substituted by methyl, carboxylic acid, a salt of carboxylic acid, a carboxylic acid ester of a $C_1$–$C_6$ alkyl, sulfonic acid, or a salt of sulfonic acid;

or $R^8$ in combination with $R^2$, or $R^9$ in combination with $R^3$, or both, form a 5- or 6-membered ring that is saturated or unsaturated, and is optionally and independently substituted one or more times by F, Cl, Br, I, CN; or $C_1$–$C_6$ alkyl, or $C_1$–$C_6$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol; sulfonic acid, or salt of sulfonic acid;

X is N—(C=Y)—$R^{10}$, N—($SO_2$)—$R^{11}$, or $CHR^{12}$;
wherein

Y is O or S;
$R^{10}$ is hydrogen, $C_1$–$C_6$ alkyl, $C_1$–$C_6$ perfluoroalkyl, $C_1$–$C_6$ alkoxy, $C_1$–$C_6$ alkenyl, aryl, amino, alkylamino, or dialkylamino, the alkyl portions of which have 1–6 carbons;

$R^{11}$ is hydrogen, $C_1$–$C_6$ alkyl, $C_1$–$C_6$ perfluoroalkyl, $C_1$–$C_6$ alkenyl, aryl, amino, alkylamino, or dialkylamino, the alkyl portions of which have 1–6 carbons;

$R^{12}$ is H, F, CN, a carboxylic acid, a salt of carboxylic acid, or a carboxylic acid ester of a $C_1$–$C_6$ alcohol; or $R^{12}$ is a saturated or unsaturated $C_1$–$C_6$ alkyl that is optionally substituted one or more times by F, Cl, Br, carboxylic acid, a salt of carboxylic acid, a carboxylic acid ester of a $C_1$–$C_6$ alcohol, a sulfonic acid, a salt of sulfonic acid, amino, alkylamino, or dialkylamino, the alkyl groups of which have 1–6 carbons; or $R^{12}$ has the formula

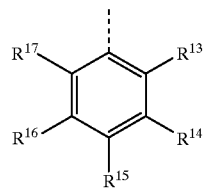

where $R^{13}$, $R^{14}$, $R^{15}$, $R^{16}$, and $R^{17}$ are independently H, F, Cl, Br, I, sulfonic acid, salt of sulfonic acid, a carboxylic acid, a salt of carboxylic acid.

2. The method, as claimed in claim 1, wherein the step of detecting comprises detecting the fluorescence emission of said detectable product.

3. The method, as claimed in claim 1, wherein the inorganic phosphate present in said reaction mixture is correlated with the presence or amount of inorganic phosphate present in said sample.

4. The method, as claimed in claim 1, wherein the inorganic phosphate present in said reaction mixture is correlated with the presence or amount of a phosphate-producing enzyme in said sample.

5. The method, as claimed in claim 4, wherein said phosphate-producing enzyme is a phosphatase enzyme.

6. The method, as claimed in claim 5, wherein said phosphatase enzyme is a nucleotide triphosphatase, a nucleotide diphosphatase, a nucleotide monophosphatase, an acid phosphatase, an alkaline phosphatase, an inositol phosphatase, or a protein phosphatase.

7. The method, as claimed in claim 5, wherein said phosphatase enzyme is an adenosine triphosphatase, a guanosine triphosphatase, an adenosine-5'-diphosphatase, a casein phosphatase, a tyrosine phosphatase, a serine phosphatase, or a threonine phosphatase.

8. The method, as claimed in claim 4, wherein said phosphate-producing enzyme is a pyrophosphatase enzyme.

9. The method, as claimed in claim 8, wherein pyrophosphate is present in said reaction mixture due to the presence of a cyclase enzyme in said sample, and the inorganic phosphate present in said reaction mixture is correlated with the presence or amount of cyclase enzyme in said sample.

10. The method, as claimed in claim 9, wherein said cyclase enzyme is an adenylyl cyclase or a guanylate cyclase.

11. The method, as claimed in claim 1, wherein one of said phosphorylase products is a phosphorylated product that is not an oxidase enzyme substrate, further comprising adding to said reaction mixture either simultaneously or sequentially a phosphatase enzyme under conditions such that said phosphatase enzyme cleaves inorganic phosphate from said phosphorylated product.

12. The method, as claimed in claim 1, wherein one of said oxidase products is a substrate for an additional oxidase enzyme, further comprising adding to said reaction mixture either simultaneously or sequentially said additional oxidase enzyme under conditions such that said additional oxidase enzyme converts said additional oxidase enzyme substrate into one or more additional oxidase products, at least one of said additional oxidase products is hydrogen peroxide.

13. The method, as claimed in claim 1, wherein said phosphorylase enzyme is a maltose phosphorylase, a trehalose phosphorylase, a sucrose phosphorylase, or a purine nucleoside phosphorylase.

14. The method, as claimed in claim 1, wherein said oxidase enzyme is a glucose oxidase or a xanthine oxidase.

15. The method, as claimed in claim 1, wherein the reaction mixture has a volume of less than or equal to 200 µL.

16. The method, as claimed in claim 15, wherein the reaction mixture is present in the well of a microplate, or on a microfluidic chip.

17. The method, as claimed in claim 1, wherein said peroxidase enzyme substrate has the formula

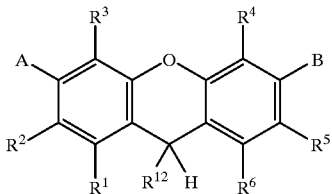

wherein $R^1$ and $R^6$ are both hydrogen;

$R^2$, $R^3$, $R^4$, and $R^5$ are independently H, F, Cl, Br, $C_1$–$C_6$ alkyl, or $C_1$–$C_6$ alkoxy;

A and B are independently OH or $NR^8R^9$, wherein
each $R^8$ and $R^9$ are independently H, or $C_1$–$C_6$ alkyl; or $R^8$ in combination with $R^9$ forms a saturated 5- or 6-membered heterocycle that is a piperidine, a morpholine, a pyrrolidine or a piperazine, each of which is optionally substituted by methyl, carboxylic acid, a salt of carboxylic acid, a carboxylic acid ester of a $C_1$–$C_6$ alkyl, sulfonic acid, or a salt of sulfonic acid;

or $R^8$ in combination with $R^2$, or $R^9$ in combination with $R^3$, or both, form a 5- or 6-membered ring that is saturated or unsaturated, and is optionally and independently substituted one or more times by F, Cl, Br, I, CN; or $C_1$–$C_6$ alkyl, or $C_1$–$C_6$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol; sulfonic acid, or salt of sulfonic acid;

$R^{12}$ has the formula

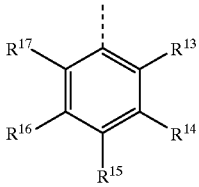

wherein $R^{13}$ is sulfonic acid, salt of sulfonic acid, a carboxylic acid, or a salt of carboxylic acid; and $R^{14}$, $R^{15}$, $R^{16}$, and $R^{17}$ are independently H, F, Cl, Br, I, sulfonic acid, salt of sulfonic acid, a carboxylic acid, or a salt of carboxylic acid.

18. The method, as claimed in claim 1, wherein said peroxidase enzyme substrate has the formula

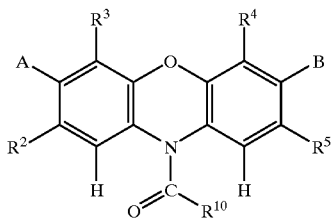

wherein $R^1$ and $R^6$ are both hydrogen;

$R^2$, $R^3$, $R^4$, and $R^5$ are independently H, F, Cl, Br, $C_1$–$C_6$ alkyl, or $C_1$–$C_6$ alkoxy;

A and B are independently OH or $NR^8R^9$; and $R^{10}$ is hydrogen or $C_1$–$C_6$ alkyl.

19. The method, as claimed in claim 18, wherein said peroxidase enzyme substrate has the formula

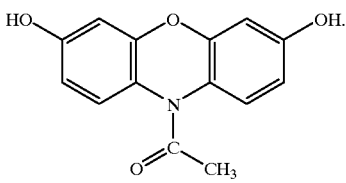

20. The method, as claimed in claim 19, wherein said phosphorylase enzyme is a maltose phosphorylase, said oxidase enzyme is a glucose oxidase, and said peroxidase enzyme is a horseradish peroxidase.

21. An assay for maltose, comprising:

a) producing a reaction mixture by treating a sample, simultaneously or sequentially, with inorganic phosphate, a maltose phosphorylase enzyme, a glucose oxidase enzyme, a peroxidase enzyme, and a peroxidase enzyme substrate under conditions such that:

when maltose is present in said reaction mixture, said maltose phosphorylase converts said inorganic phosphate and maltose into glucose and glucose-1-phosphate;

said glucose oxidase converts said glucose into oxidase products, at least one of which is hydrogen peroxide;

in the presence of hydrogen peroxide, said peroxidase enzyme converts said peroxidase enzyme substrate into a detectable product;

b) detecting the presence or amount of said detectable product in said reaction mixture; and c) correlating the presence or amount of said detectable product in said reaction mixture with the presence or amount of maltose in said reaction mixture;

wherein said peroxidase enzyme substrate has the formula

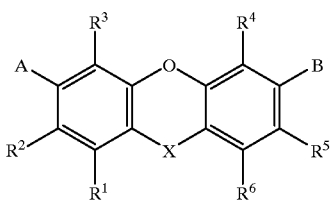

wherein $R^2$, $R^3$, $R^4$ and $R^5$ are independently H, F, Cl, Br, I, CN; or $C_1$–$C_6$ alkyl, or $C_1$–$C_6$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol, sulfonic acid, or a salt of sulfonic acid;

$R^1$ and $R^6$ are H; or $R^1$ taken in combination with $R^2$, or $R^5$ taken in combination with $R^6$, or both, form a fused aromatic six membered ring that is optionally and independently substituted one or more times by F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol, sulfonic acid, or a salt of sulfonic acid;

A and B are independently OH or $NR^8R^9$, wherein each $R^8$ and $R^9$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alcohol; or $R^8$ in combination with $R^9$ forms a saturated 5- or 6-membered heterocycle that is a piperidine, a morpholine, a pyrrolidine or a piperazine, each of which is optionally substituted by methyl, carboxylic acid, a salt of carboxylic acid, a carboxylic acid ester of a $C_1$–$C_6$ alkyl, sulfonic acid, or a salt of sulfonic acid;

or $R^8$ in combination with $R^2$, or $R^9$ in combination with $R^3$, or both, form a 5- or 6-membered ring that is saturated or unsaturated, and is optionally and independently substituted one or more times by F, Cl, Br, I, CN; or $C_1$–$C_6$ alkyl, or $C_1$–$C_6$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol; sulfonic acid, or salt of sulfonic acid;

X is N—(C=Y)—$R^{10}$, N—($SO_2$)—$R^{11}$, or $CHR^{12}$; wherein

Y is O or S;

$R^{10}$ is hydrogen, $C_1$–$C_6$ alkyl, $C_1$–$C_6$ perfluoroalkyl, $C_1$–$C_6$ alkoxy, $C_1$–$C_6$ alkenyl, aryl, amino, alkylamino, or dialkylamino, the alkyl portions of which have 1–6 carbons;

$R^{11}$ is hydrogen, $C_1$–$C_6$ alkyl, $C_1$–$C_6$ perfluoroalkyl, $C_1$–$C_6$ alkenyl, aryl, amino, alkylamino, or dialkylamino, the alkyl portions of which have 1–6 carbons;

$R^{12}$ is H, F, CN, a carboxylic acid, a salt of carboxylic acid, or a carboxylic acid ester of a $C_1$–$C_6$ alcohol; or $R^{12}$ is a saturated or unsaturated $C_1$–$C_6$ alkyl that is optionally substituted one or more times by F, Cl, Br, carboxylic acid, a salt of carboxylic acid, a carboxylic acid ester of a $C_1$–$C_6$ alcohol, a sulfonic acid, a salt of sulfonic acid, amino, alkylamino, or dialkylamino, the alkyl groups of which have 1–6 carbons; or $R^{12}$ has the formula

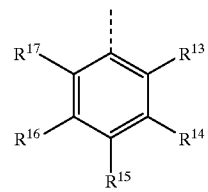

where $R^{13}$, $R^{14}$, $R^{15}$, $R^{16}$, and $R^{17}$ are independently H, F, Cl, Br, I, sulfonic acid, salt of sulfonic acid, a carboxylic acid, a salt of carboxylic acid.

22. The method, as claimed in claim 21, wherein the step of detecting comprises detecting the fluorescence emission of said detectable product.

23. The method, as claimed in claim 21, wherein the maltose present in said reaction mixture is correlated with the presence or amount of maltose present in said sample.

24. An assay for a phosphate-producing enzyme, comprising:

a) producing a reaction mixture by treating a sample, simultaneously or sequentially, with an appropriate substrate for said phosphate-producing enzyme, a phosphorylase enzyme, a phosphorylase enzyme substrate, an oxidase enzyme, a peroxidase enzyme, and a peroxidase enzyme substrate under conditions such that:

when said phosphate-producing enzyme is present in said reaction mixture, said phosphate-producing enzyme converts said phosphate-producing enzyme substrate into one or more products, at least one of which is inorganic phosphate;

said phosphorylase enzyme converts said inorganic phosphate and said phosphorylase enzyme substrate into one or more phosphorylase products, at least one of which is an oxidase substrate for said oxidase enzyme;

said oxidase enzyme converts said oxidase substrate into one or more oxidase products, at least one of which is hydrogen peroxide;

in the presence of hydrogen peroxide, said peroxidase enzyme converts said peroxidase enzyme substrate into a detectable product;

b) detecting the presence or amount of said detectable product in said reaction mixture; and c) correlating the presence or amount of said detectable product in said reaction mixture with the presence or amount of phosphate-producing enzyme in said reaction mixture;

wherein said peroxidase enzyme substrate has the formula

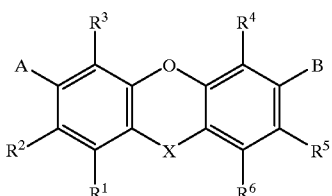

wherein
$R^2$, $R^3$, $R^4$ and $R^5$ are independently H, F, Cl, Br, I, CN; or $C_1$–$C_6$ alkyl, or $C_1$–$C_6$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol, sulfonic acid, or a salt of sulfonic acid;

$R^1$ and $R^6$ are H; or $R^1$ taken in combination with $R^2$, or $R^5$ taken in combination with $R^6$, or both, form a fused aromatic six membered ring that is optionally and independently substituted one or more times by F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol, sulfonic acid, or a salt of sulfonic acid;

A and B are independently OH or $NR^8R^9$, wherein each $R^8$ and $R^9$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alcohol; or $R^8$ in combination with $R^9$ forms a saturated 5- or 6-membered heterocycle that is a piperidine, a morpholine, a pyrrolidine or a piperazine, each of which is optionally substituted by methyl, carboxylic acid, a salt of carboxylic acid, a carboxylic acid ester of a $C_1$–$C_6$ alkyl, sulfonic acid, or a salt of sulfonic acid;

or $R^8$ in combination with $R^2$, or $R^9$ in combination with $R^3$, or both, form a 5- or 6-membered ring that is saturated or unsaturated, and is optionally and independently substituted one or more times by F, Cl, Br, I, CN; or $C_1$–$C_6$ alkyl, or $C_1$–$C_6$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol; sulfonic acid, or salt of sulfonic acid;

X is N—(C=Y)—$R^{10}$, N—($SO_2$)—$R^{11}$, or $CHR^{12}$; wherein
Y is O or S;
$R^{10}$ is hydrogen, $C_1$–$C_6$ alkyl, $C_1$–$C_6$ perfluoroalkyl, $C_1$–$C_6$ alkoxy, $C_1$–$C_6$ alkenyl, aryl, amino, alkylamino, or dialkylamino, the alkyl portions of which have 1–6 carbons;
$R^{11}$ is hydrogen, $C_1$–$C_6$ alkyl, $C_1$–$C_6$ perfluoroalkyl, $C_1$–$C_6$ alkenyl, aryl, amino, alkylamino, or dialkylamino, the alkyl portions of which have 1–6 carbons;
$R^{12}$ is H, F, CN, a carboxylic acid, a salt of carboxylic acid, or a carboxylic acid ester of a $C_1$–$C_6$ alcohol; or $R^{12}$ is a saturated or unsaturated $C_1$–$C_6$ alkyl that is optionally substituted one or more times by F, Cl, Br, carboxylic acid, a salt of carboxylic acid, a carboxylic acid ester of a $C_1$–$C_6$ alcohol, a sulfonic acid, a salt of sulfonic acid, amino, alkylamino, or dialkylamino, the alkyl groups of which have 1–6 carbons; or $R^{12}$ has the formula

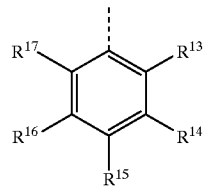

where $R^{13}$, $R^{14}$, $R^{15}$, $R^{16}$, and $R^{17}$ are independently H, F, Cl, Br, I, sulfonic acid, salt of sulfonic acid, a carboxylic acid, a salt of carboxylic acid.

25. The method, as claimed in claim 24, wherein the step of detecting comprises detecting the fluorescence emission of said detectable product; and the presence or amount of phosphate-producing enzyme present in said reaction mixture is correlated with the presence or amount of a phosphate-producing enzyme in said sample.

26. The method, as claimed in claim 24, wherein said phosphate-producing enzyme is a pyrophosphatase enzyme.

27. The method, as claimed in claim 24, wherein said phosphorylase enzyme, said oxidase enzyme, and said peroxidase enzyme are added to said sample prior to the addition of said peroxidase enzyme substrate, and further comprising:
  a) adding to the reaction mixture a catalase enzyme;
  b) incubating said sample under conditions such that any inorganic phosphate present in said reaction mixture to be converted to hydrogen peroxide, and subsequently eliminated by said catalase enzyme; and
  c) separating said catalase enzyme from the reaction mixture prior to adding said peroxidase enzyme substrate to said reaction mixture.

28. The method, as claimed in claim 27, wherein at least one of said phosphorylase enzyme, oxidase enzyme, and catalase enzyme is immobilized on a polymeric matrix.

29. A composition comprising:
  a) a phosphorylase enzyme;
  b) a phosphorylase enzyme substrate;
  c) an oxidase enzyme;
  d) a peroxidase enzyme; and
  e) a peroxidase enzyme substrate;
    each selected such that under appropriate conditions including the presence of inorganic phosphate, said phosphorylase enzyme converts said inorganic phosphate and said phosphorylase enzyme substrate into one or more phosphorylase products, at least one of which is an oxidase substrate for said oxidase enzyme;
    said oxidase enzyme converts said oxidase substrate into one or more oxidase products, at least one of which is hydrogen peroxide; and
    in the presence of hydrogen peroxide, said peroxidase enzyme converts said peroxidase enzyme substrate into a detectable product;
  wherein said peroxidase enzyme substrate has the formula

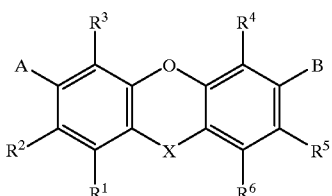

wherein

R², R³, R⁴ and R⁵ are independently H, F, Cl, Br, I, CN; or $C_1$–$C_6$ alkyl, or $C_1$–$C_6$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol, sulfonic acid, or a salt of sulfonic acid;

R¹ and R⁶ are H; or R¹ taken in combination with R², or R⁵ taken in combination with R⁶, or both, form a fused aromatic six membered ring that is optionally and independently substituted one or more times by F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol, sulfonic acid, or a salt of sulfonic acid;

A and B are independently OH or NR⁸R⁹, wherein each R⁸ and R⁹ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alcohol; or R⁸ in combination with R⁹ forms a saturated 5- or 6-membered heterocycle that is a piperidine, a morpholine, a pyrrolidine or a piperazine, each of which is optionally substituted by methyl, carboxylic acid, a salt of carboxylic acid, a carboxylic acid ester of a $C_1$–$C_6$ alkyl, sulfonic acid, or a salt of sulfonic acid;

or R⁸ in combination with R², or R⁹ in combination with R³, or both, form a 5- or 6-membered ring that is saturated or unsaturated, and is optionally and independently substituted one or more times by F, Cl, Br, I, CN; or $C_1$–$C_6$ alkyl, or $C_1$–$C_6$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol; sulfonic acid, or salt of sulfonic acid;

X is N—(C=Y)—R¹⁰, N—(SO₂)—R¹¹, or CHR¹²; wherein

Y is O or S;

R¹⁰ is hydrogen, $C_1$–$C_6$ alkyl, $C_1$–$C_6$ perfluoroalkyl, $C_1$–$C_6$ alkoxy, $C_1$–$C_6$ alkenyl, aryl, amino, alkylamino, or dialkylamino, the alkyl portions of which have 1–6 carbons;

R¹¹ is hydrogen, $C_1$–$C_6$ alkyl, $C_1$–$C_6$ perfluoroalkyl, $C_1$–$C_6$ alkenyl, aryl, amino, alkylamino, or dialkylamino, the alkyl portions of which have 1–6 carbons;

R¹² is H, F, CN, a carboxylic acid, a salt of carboxylic acid, or a carboxylic acid ester of a $C_1$–$C_6$ alcohol; or R¹² is a saturated or unsaturated $C_1$–$C_6$ alkyl that is optionally substituted one or more times by F, Cl, Br, carboxylic acid, a salt of carboxylic acid, a carboxylic acid ester of a $C_1$–$C_6$ alcohol, a sulfonic acid, a salt of sulfonic acid, amino, alkylamino, or dialkylamino, the alkyl groups of which have 1–6 carbons; or R¹² has the formula

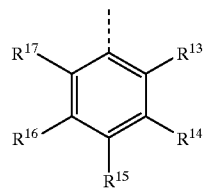

where R¹³, R¹⁴, R¹⁵, R¹⁶, and R¹⁷ are independently H, F, Cl, Br, I, sulfonic acid, salt of sulfonic acid, a carboxylic acid, a salt of carboxylic acid.

30. The composition, as claimed in claim 29, further comprising one or more buffering agents or metal salts.

31. The composition, as claimed in claim 29, further comprising a pyrophosphatase enzyme.

32. The composition, as claimed in claim 29, further comprising inorganic phosphate.

33. The composition, as claimed in claim 29, further comprising one or more nucleotides, sugar phosphates, phosphorylated proteins, inositol phosphates, or creatine phosphates.

34. The composition, as claimed in claim 29, further comprising a biological or environmental sample.

35. The composition, as claimed in claim 29, wherein said biological sample is a biological fluid, a cell lysate, or a culture medium.

36. The composition, as claimed in claim 29, wherein said phosphorylase enzyme is a purine nucleoside phosphorylase, said oxidase enzyme is a xanthine oxidase, said peroxidase enzyme is a horseradish peroxidase, and further comprising inosine or xanthosine.

37. The composition, as claimed in claim 29, wherein said phosphorylase enzyme is a maltose phosphorylase, said oxidase enzyme is a glucose oxidase, said peroxidase enzyme is a horseradish peroxidase, and further comprising maltose.

38. The kit, comprising:

a) a phosphorylase enzyme;

b) a phosphorylase enzyme substrate;

c) an oxidase enzyme;

d) a peroxidase enzyme; and e) a peroxidase enzyme substrate;

each selected such that under appropriate conditions including the presence of inorganic phosphate, said phosphorylase enzyme converts said inorganic phosphate and said phosphorylase enzyme substrate into one or more phosphorylase products, at least one of which is an oxidase substrate for said oxidase enzyme;

said oxidase enzyme converts said oxidase substrate into one or more oxidase products, at least one of which is hydrogen peroxide; and in the presence of hydrogen peroxide, said peroxidase enzyme converts said peroxidase enzyme substrate into a detectable product;

wherein said peroxidase enzyme substrate has the formula

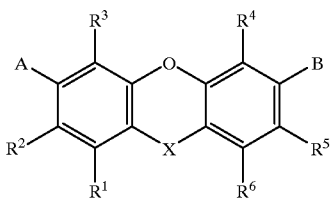

wherein
$R^2$, $R^3$, $R^4$ and $R^5$ are independently H, F, Cl, Br, I, CN; or $C_1$–$C_6$ alkyl, or $C_1$–$C_6$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol, sulfonic acid, or a salt of sulfonic acid;

$R^1$ and $R^6$ are H; or $R^1$ taken in combination with $R^2$, or $R^5$ taken in combination with $R^6$, or both, form a fused aromatic six membered ring that is optionally and independently substituted one or more times by F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol, sulfonic acid, or a salt of sulfonic acid;

A and B are independently OH or $NR^8R^9$, wherein each $R^8$ and $R^9$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alcohol; or $R^8$ in combination with $R^9$ forms a saturated 5- or 6-membered heterocycle that is a piperidine, a morpholine, a pyrrolidine or a piperazine, each of which is optionally substituted by methyl, carboxylic acid, a salt of carboxylic acid, a carboxylic acid ester of a $C_1$–$C_6$ alkyl, sulfonic acid, or a salt of sulfonic acid;

or $R^8$ in combination with $R^2$, or $R^9$ in combination with $R^3$, or both, form a 5- or 6-membered ring that is saturated or unsaturated, and is optionally and independently substituted one or more times by F, Cl, Br, I, CN; or $C_1$–$C_6$ alkyl, or $C_1$–$C_6$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol; sulfonic acid, or salt of sulfonic acid;

X is N—(C=Y)—$R^{10}$, N—($SO_2$)—$R^{11}$, or $CHR^{12}$; wherein
Y is O or S;
$R^{10}$ is hydrogen, $C_1$–$C_6$ alkyl, $C_1$–$C_6$ perfluoroalkyl, $C_1$–$C_6$ alkoxy, $C_1$–$C_6$ alkenyl, aryl, amino, alkylamino, or dialkylamino, the alkyl portions of which have 1–6 carbons;
$R^{11}$ is hydrogen, $C_1$–$C_6$ alkyl, $C_1$–$C_6$ perfluoroalkyl, $C_1$–$C_6$ alkenyl, aryl, amino, alkylamino, or dialkylamino, the alkyl portions of which have 1–6 carbons;
$R^{12}$ is H, F, CN, a carboxylic acid, a salt of carboxylic acid, or a carboxylic acid ester of a $C_1$–$C_6$ alcohol; or $R^{12}$ is a saturated or unsaturated $C_1$–$C_6$ alkyl that is optionally substituted one or more times by F, Cl, Br, carboxylic acid, a salt of carboxylic acid, a carboxylic acid ester of a $C_1$–$C_6$ alcohol, a sulfonic acid, a salt of sulfonic acid, amino, alkylamino, or dialkylamino, the alkyl groups of which have 1–6 carbons; or $R^{12}$ has the formula

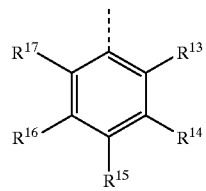

where $R^{13}$, $R^{14}$, $R^{15}$, $R^{16}$, and $R^{17}$ are independently H, F, Cl, Br, I, sulfonic acid, salt of sulfonic acid, a carboxylic acid, a salt of carboxylic acid.

39. The kit, as claimed in claim 38, further comprising a pyrophosphatase enzyme.

40. The kit, as claimed in claim 38, further comprising inorganic phosphate.

41. The kit, as claimed in claim 38, further comprising the detectable product.

42. The kit, as claimed in claim 38, wherein said phosphorylase enzyme is a purine nucleoside phosphorylase, said oxidase enzyme is a xanthine oxidase, and said peroxidase enzyme is a horseradish peroxidase.

43. The kit, as claimed in claim 38, wherein said phosphorylase enzyme is a maltose phosphorylase, said oxidase enzyme is a glucose oxidase, and said peroxidase enzyme is a horseradish peroxidase.

44. The kit, as claimed in claim 43, further comprising maltose that is essentially glucose-free.

45. The kit, as claimed in claim 38, wherein said peroxidase enzyme substrate has the formula

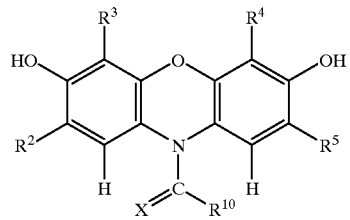

wherein X is O or S;
$R^1$ and $R^6$ are both hydrogen;
$R^2$, $R^3$, $R^4$, and $R^5$ are independently H, F, Cl, Br, $C_1$–$C_6$ alkyl, or $C_1$–$C_6$ alkoxy; and
$R^{10}$ is hydrogen or $C_1$–$C_6$ alkyl.

46. The kit, as claimed in claim 45, wherein said peroxidase enzyme substrate has the formula

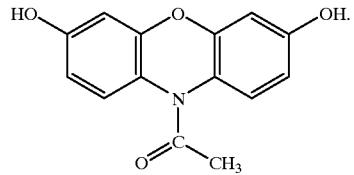

* * * * *